United States Patent
Bhugra et al.

(10) Patent No.: US 12,370,340 B2
(45) Date of Patent: Jul. 29, 2025

(54) BRAIN COMPUTER INTERFACE BASED PAIN MANAGEMENT THERAPY

(71) Applicant: NeuroLutions, Inc., Santa Cruz, CA (US)

(72) Inventors: Kern Bhugra, Santa Cruz, CA (US); Eric C. Leuthardt, St. Louis, MO (US)

(73) Assignee: NeuroLutions, Inc., Santa Cruz, CA (US)

( * ) Notice: Subject to any disclaimer, the term of this patent is extended or adjusted under 35 U.S.C. 154(b) by 818 days.

(21) Appl. No.: 16/521,056

(22) Filed: Jul. 24, 2019

(65) Prior Publication Data

US 2021/0023330 A1 Jan. 28, 2021

(51) Int. Cl.
| | |
|---|---|
| A61M 21/02 | (2006.01) |
| A61B 5/377 | (2021.01) |
| A61B 5/383 | (2021.01) |
| A61M 21/00 | (2006.01) |

(52) U.S. Cl.
CPC .............. *A61M 21/02* (2013.01); *A61B 5/377* (2021.01); *A61B 5/383* (2021.01); *A61M 2021/0022* (2013.01); *A61M 2021/0066* (2013.01); *A61M 2205/05* (2013.01); *A61M 2205/3606* (2013.01); *A61M 2205/3673* (2013.01); *A61M 2205/50* (2013.01); *A61M 2205/52* (2013.01); *A61M 2230/10* (2013.01)

(58) Field of Classification Search
CPC .......... A61M 21/02; A61M 2021/0066; A61M 2205/05; A61M 2205/3606; A61M 2205/3673; A61M 2021/0022; A61M 2230/10; A61B 5/375–377

USPC ........................................................ 601/46
See application file for complete search history.

(56) References Cited

U.S. PATENT DOCUMENTS

| | | | | |
|---|---|---|---|---|
| 2010/0249637 | A1* | 9/2010 | Walter | A61H 23/02 601/46 |
| 2015/0174362 | A1* | 6/2015 | Panova | G16H 10/60 600/27 |
| 2015/0294074 | A1 | 10/2015 | Kawato | |
| 2017/0352283 | A1 | 12/2017 | Lau | |
| 2019/0314599 | A1* | 10/2019 | Schneider | G06F 17/00 |

(Continued)

FOREIGN PATENT DOCUMENTS

| | | |
|---|---|---|
| CN | 1736327 A | 2/2006 |
| CN | 1887375 A | 1/2007 |
| CN | 101677775 A | 3/2010 |

(Continued)

OTHER PUBLICATIONS

Decharms et al., "Control Over Brain Activation and Pain Learned by Using Real Time Functional MRI", Proceedings of the National Academy of Sciences, No. 51, dated Dec. 20, 2005, 5 pages.

(Continued)

*Primary Examiner* — Thaddeus B Cox
(74) *Attorney, Agent, or Firm* — Fish & Richardson P.C.

(57) ABSTRACT

Systems, devices and methods are provided for conducting a pain management therapy session, which includes performing a BCI training session utilizing feedback to train a subject to generate defined brain signals to assist the subject in managing and/or relieving pain, and applying a stimulus to the subject, in connection with the BCI training session, at a location that is near the source of pain and/or within the nervous system pain pathway to the source of pain.

10 Claims, 7 Drawing Sheets

(56) References Cited

U.S. PATENT DOCUMENTS

2020/0069208 A1\* 3/2020 Keane .................. A61B 5/742

FOREIGN PATENT DOCUMENTS

| CN | 106793955 A | 5/2017 |
|---|---|---|
| WO | WO 2004103230 | 12/2004 |
| WO | WO-2018059645 A1 \* | 4/2018 |

OTHER PUBLICATIONS

PCT International Search Report and Written Opinion in the PCT Appln No. PCT/US2020/042879, dated Jul. 21, 2020, 18 pages.
International Preliminary Report on Patentability in International Appln. No. PCT/US2020/042879, dated Feb. 3, 2022, 10 pages.

\* cited by examiner

BRAIN COMPUTER INTERFACE BASED PAIN MANAGEMENT THERAPY

TECHNICAL FIELD

This document relates to pain management therapy utilizing brain computer interface (BCI) techniques.

BACKGROUND

Pain management is a discipline for easing the suffering and improving the quality of life of those living with chronic pain. Various therapies have been developed to address pain, including drug and device therapies. Each of the various therapies has drawbacks. New techniques of pain management are needed.

Brain computer interface ("BCI") technology is a technological field in which intentions present in brain signals are acquired and harnessed to perform various functions. BCI technology has been explored for use in the field of pain management but further development in the field is needed to produce viable pain management therapy devices and methods utilizing BCI technology.

SUMMARY

This document describes systems, devices, and methods for performing pain management therapy utilizing BCI techniques, and a stimulation device that is provided to the subject experiencing pain at a location that is local to the source of pain and/or within the pain pathway.

In one aspect, systems, devices and methods are provided for conducting a pain management therapy session, which session includes performing a BCI training session utilizing feedback to train a subject to generate defined brain signals to assist the subject in managing and/or relieving pain, and applying a stimulus to the subject, in connection with the BCI training session, at a location that is near the source of pain and/or within the nervous system pain pathway to the source of pain.

In various implementations, the BCI training session may be designed and configured to train the patient to generate an increase in the power of the alpha rhythm brain waves as compared to a power level of the alpha rhythm brain wave baseline measure. In this case, the stimulus applied to the subject may generate a source of pain or discomfort to the subject, for example, the stimulus may comprise a cold temperature stimulus, for example a cold inducing element such as a Peltier cooling device.

Alternatively or additionally, the BCI training session may be designed and configured to train the patient to generate a decrease in the power of the alpha rhythm brain waves as compared to a power level of the alpha rhythm brain wave baseline measure. In this case, the stimulus applied to subject may comprise a source of relief or soothing feeling and/or a procioceptive stimulus. For example, the stimulus applied to the subject is generated by a vibration generating element such as a wearable vibration generating element.

In other aspects, systems and devices are provided for conducting a pain management therapy session, including a brain signal acquisition system for continuously acquiring brain signals from multiple locations of a subject's brain, a stimulation device configured and adapted to be applied to the subject at a location within a pain pathway of a source of pain, and a brain computer interface (BCI) control/processing module programmed to train the subject, utilizing the stimulation device, to generate define brain signals selected to assist the subject in managing and/or relieving pain.

In yet additional aspects, systems, devices and methods are provided to utilize BCI techniques and a stimulation device to manage and/or relieve pain after one or more therapy sessions, as shown and described.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document relates to managing and/or relieving pain in a subject such as a person or animal, particularly but not exclusively, managing and/or relieving chronic pain. In various embodiments, the devices, systems, and methods disclosed herein utilize brain computer interface (BCI) techniques in pain management therapy and/or on-going management of pain after such therapy.

Generally, this document relates to pain management therapy to assist a subject in managing pain. For example, this document describes various methods of applying a stimulus, such as an external stimulus, to a location of the subject's body that is located near a source of pain and/or within a pain pathway to the source of pain. While applying the stimulus, continuously acquired brain signals are evaluated while providing feedback to the patient, wherein the feedback is designed and configured to train the patient to generate defined brain signals selected to assist the subject in managing pain.

This document also describes various systems and devices for conducting a pain management therapy session. Generally, such a system may include a brain signal acquisition system (with electrodes) for continuously acquiring brain signals from multiple locations of a subject's brain, a stimulation device configured and adapted to be applied to the subject at a location within a pain pathway of a source of pain, and a brain computer interface (BCI) control/processing module programmed to train the subject to generate define brain signals selected to assist the subject in managing pain of a subject's brain.

Figure 1A:
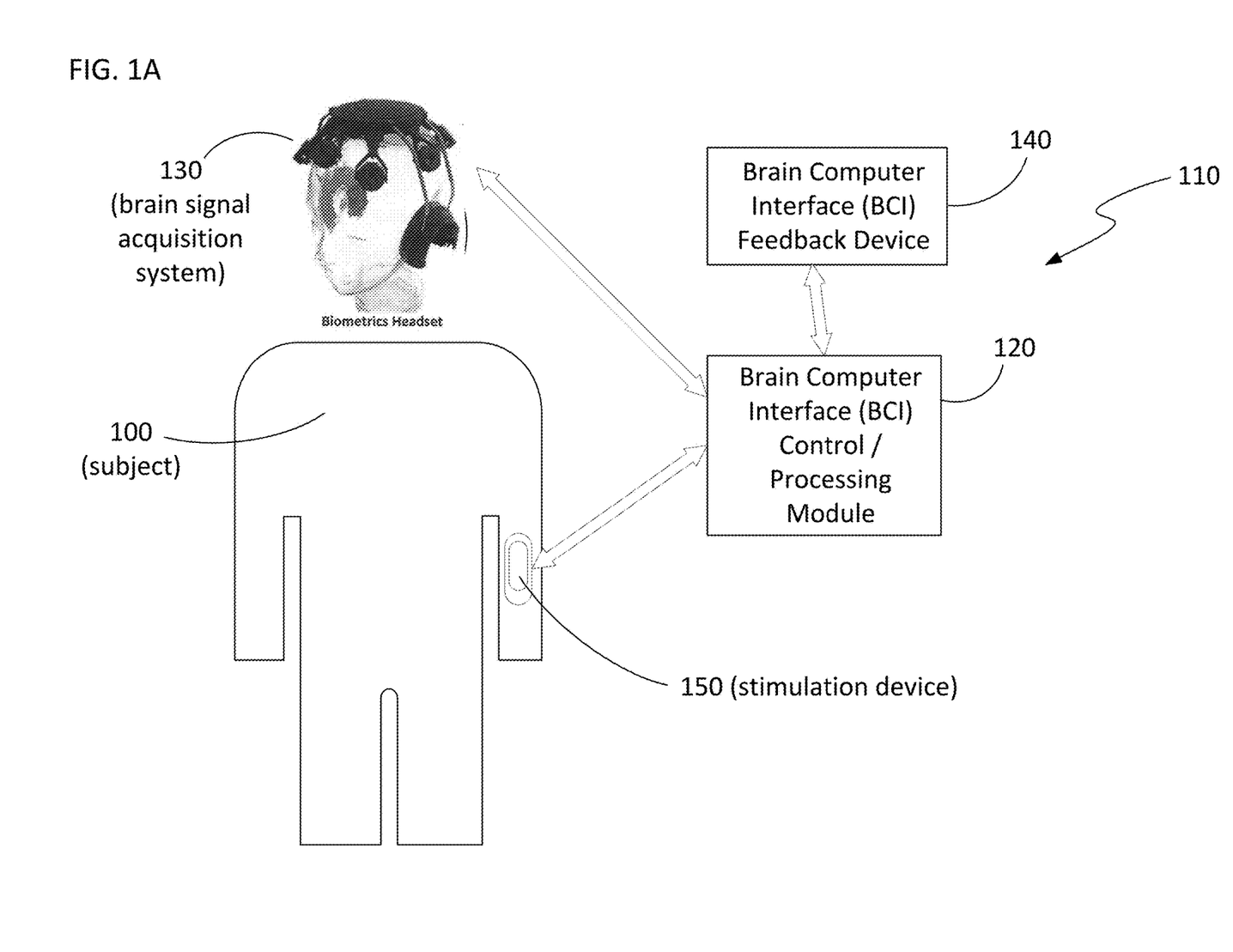
FIG. 1A is a diagram of a system for managing pain in a subject including a therapy session utilizing brain computer interface (BCI) techniques having as its goal enabling the subject to manage pain, for example, chronic pain.

As an illustration of these methods and systems for pain management, FIG. 1 shows a subject (in this case a human subject) 100 and a system 110 for managing pain which may be used, for example, in a therapy session utilizing BCI techniques to provide the subject 100 with the ability to manage and/or relieve pain. The system 110 in this example includes a BCI control/processing module 120 communicatively coupled with a brain signal acquisition system 130, a BCI training feedback device 140, and a stimulation device 150 which in this example is a body worn external stimulation device. In some embodiments, the stimulation device is adapted and configured to provide a stimulus to the patient that is unrelated to continuously acquired brain signals that may be used by themselves as in a BCI training process. In other embodiments, the stimulation device 150 may—alternatively or in addition to the feedback device 140—serve as a BCI training feedback device.

The brain signal acquisition system 130, in this example, is an external headset having skin surface electrodes that acquire electroencephalogram (EEG) brain signals from multiple different and distributed surface locations on the subject's skin adjacent the brain. The brain signal acquisition system 130 may be a commercially available brain signal acquisition headset. The brain signal acquisition system 130 acquires brain signals, performs low-level signal processing, and transmit the EEG brain signals (for example, wirelessly) for receipt by the BCI control/processing module 120. The EEG brain signals are acquired by the acquisition system 130 using a number of arranged surface electrodes that are part of the acquisition system 130. Each of the surface electrodes may be located at an end of a corresponding arm that extends from a housing of the acquisition system 130 to a distal position such that, when the acquisition system 130 is worn by the patient, the electrodes may be positioned to rest upon the patient's skin adjacent the brain. The electrodes may be dry electrodes or alternatively may be moistened, through application of a liquid or gel applied to the electrodes, before being applied to the patient's skin, in order to ensure adequate conductivity with the patient's skin to allow for brain signals to be detected and recorded with sufficient accuracy.

The brain signal acquisition system 130 may be configured so that the electrodes may be positioned generally on all surfaces of the skin adjacent the subject's brain or alternatively may be designed to provide electrode contact to acquire signals from particular locations of the brain relevant to the techniques described herein. Although an EEG-based brain signal acquisition system 130 with skin surface electrodes is shown in the FIG. 1 example, other brain signal acquisition systems may alternatively be used. For example, acquisition systems with implantable electrodes may be used. For example, electrocorticography (ECOG) electrodes may be used and implanted under the skull of the patient and positioned so that the electrodes rest upon the brain surface but without penetrating into the brain tissue. Another example electrode system that may alternatively be used is a "point-style" electrode system that is also implanted beneath the skull of the patient, although this type of electrode system has electrode tips that penetrate into the brain tissue. Typically, such "point-style" implanted electrode systems include many prongs designed so that each of the prongs penetrates into the brain tissue at a different location.

A brain signal acquisition system that has implantable electrodes—wherein the acquisition system is entirely implantable or wherein only the electrodes and leads thereto are implantable—may be desirable over an acquisition system with only surface EEG electrodes in that with implanted electrodes the acquired brain signals may contain greater information content regarding the intentions of the patient. That is because the skull may operate to block a portion of information in the brain signals, particularly at higher frequencies. That said, it will be recognized that implantable electrodes have the potential drawback of requiring a medical procedure to implant the electrodes.

Figure 1B:
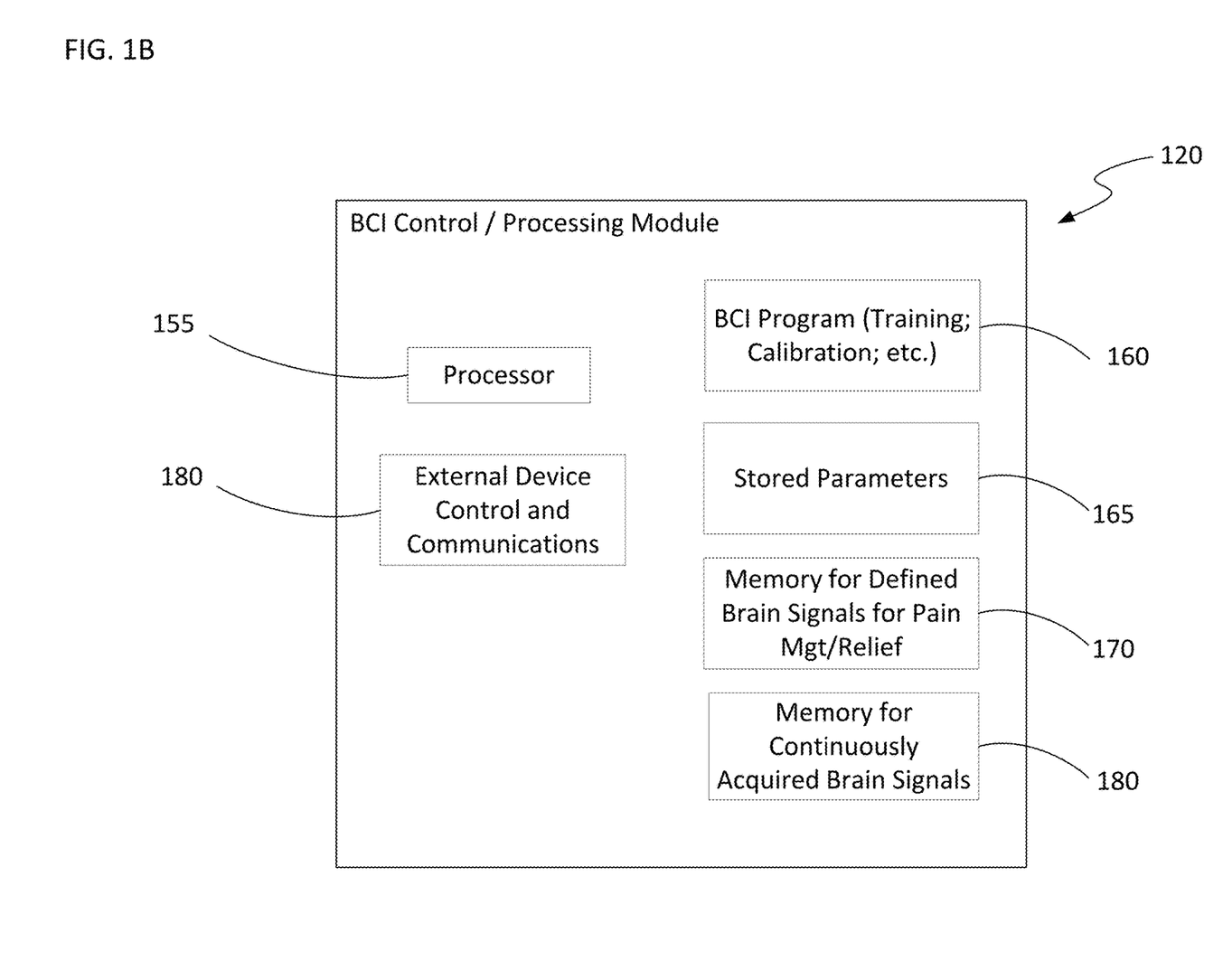
FIG. 1B is a block diagram of a BCI control/processing module for use in the system of FIG. 1A.

The BCI control/processing module 120 is generally adapted to receive wirelessly transmitted signals containing information about the brain signals acquired by the acquisition system 130, process those received signals to determine for example the power levels of certain defined brain signals (and/or brain rhythms) and/or determine subject intentions, and depending upon the nature of the brain signals, cause a response to be made by the BCI feedback device 140 and/or the stimulation device 150. To do this as shown in FIG. 1B, the BCI control/processing module 120 includes known BCI processing and control capability, for example, and would include the ability to provide control signals to control operation of the feedback device 140 and/or the stimulation device 150. In addition, the BCI control/processing module 120 may be adapted to be attached to and/or worn by the subject or may reside on a separate computing device not designed to be worn by the subject.

The BCI feedback device 140 may be a visual display under control of the BCI control/processing module 120, which feedback device 140 the subject is able to see when performing a pain therapy session. For example, the BCI feedback device 140 may provide various visual displays useful in training the patient to produce certain desired brain signals, such as those commonly used in the BCI field (e.g., cursor or object location on a video screen and movement of that cursor/object) or that may be developed in the future. In various embodiments, the feedback device 140 may provide other forms of feedback such as auditory (sound) feedback signals and/or haptic feedback signals (e.g., vibrational, motion or other forces sensed by the subject's sense of touch).

The stimulation device 150 may be a body-worn patch type device as shown in the FIG. 1 example, designed to be affixed to and worn by the subject. The stimulation device 150 may be applied to the patient, as will be described later, at a location that is local to the source of pain the subject is receiving and/or positioned so that is within the pain pathway to the source of pain. In various embodiments, the stimulation device 150 may be a device that generates heat and/or cooling. As one example, a controllable cool temperature may be generated by a Peltier device provided with the stimulation device such that the stimulation device 150 provides an uncomfortable or painful sensation to the patient when applied to the surface of the subject's skin. Controlling the temperature may then control the degree of pain being applied to the patient. A heat generating device may operate similarly.

In other embodiments, the stimulation device 150 may alternatively or additionally include a vibrational device that produces vibration that is felt at the skin adjacent where the stimulation device 150 is worn. The stimulation device 150 with vibrational capability may be designed such that the vibrational motion as applied to the subject is of sufficient magnitude and design that it may direct the patient's thoughts away from chronic pain sensation and toward more soothing vibrational sensations. In this sense, the stimulation device provides not a source of discomfort and/or pain as with a Peltier and/or heat generating device, but rather provides a source of comfort and/or distraction from the pain.

FIG. 1B shows further detail of the BCI control/processing module 120. The module 120 includes a processor 155 and BCI program 160 to perform the functions described below required of the BCI control/processing module 120. The BCI control/processing module further includes memory 165 to store parameters related to BCI functions and other operating conditions for a particular subject, memory 170 to store defined brain signals that may be acquired and determined for a subject and that may assist a subject in managing and/or relieving pain, and memory 180 to store continuously acquired brain signals, as will be described below. During a BCI pain management therapy session, the processor 155 executes code instructions making up the BCI program 160 to perform, among other things, a comparison of the continuously acquired brain signals to the defined brain signals that will be useful in managing and/or relieving pain. The BCI control/processing module 120 also includes external device control and communications devices 180 to communicate with and or send control signals to and from (by wireless or hardwired communication) the brain signal acquisition system 130, the BCI feedback device 140, and the stimulation device 150.

Figure 2:
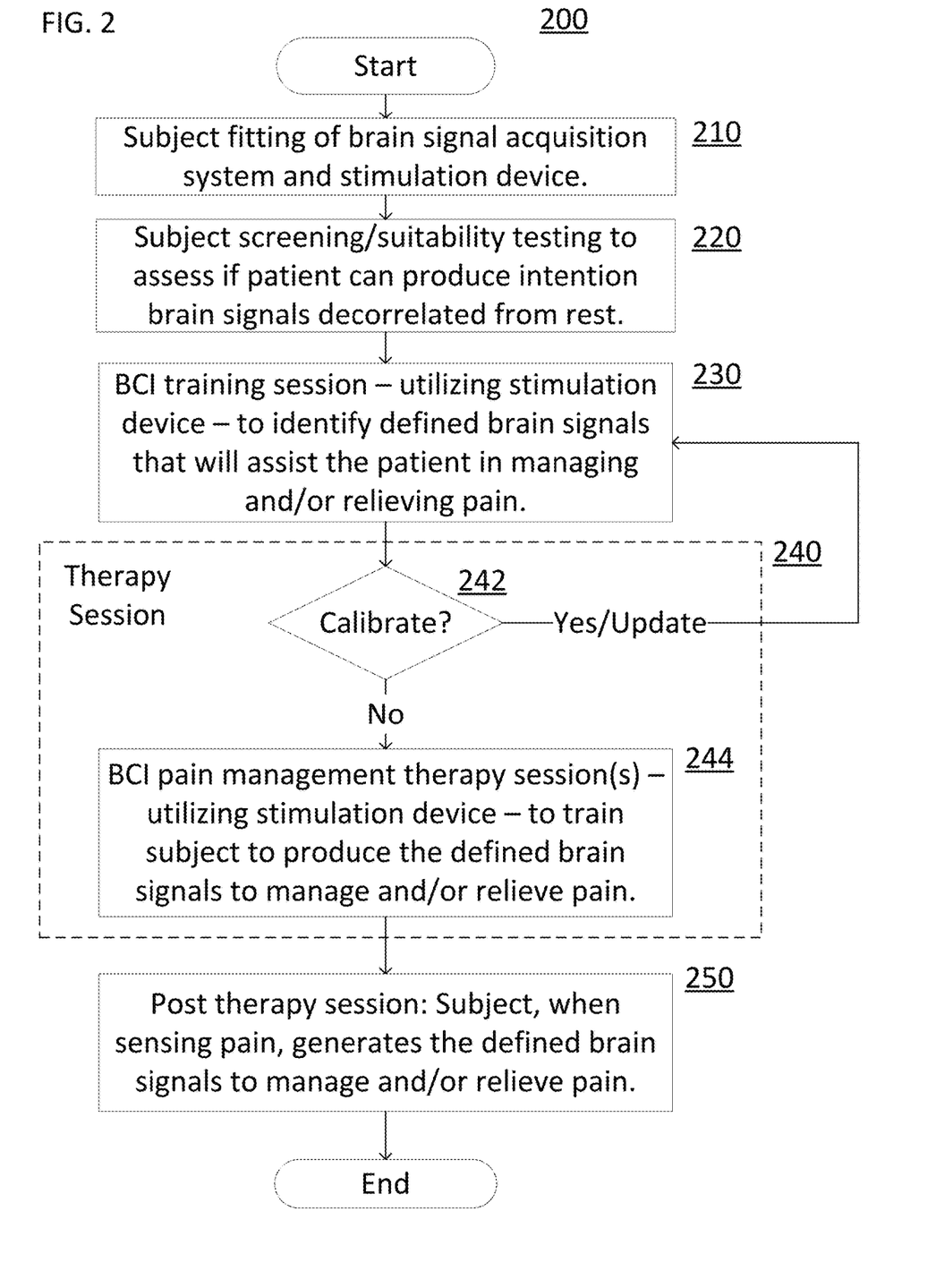
FIG. 2 is a flowchart illustrating an example method for managing a subject's pain including a method for conducting a therapy session utilizing brain computer interface (BCI) techniques.

Referring now to FIG. 2, there is shown a flowchart describing at a high level a method 200 of a subject managing pain, for example, chronic pain. First at 210 the subject may be fitted with a suitable brain signal acquisition system and stimulation device. At 220 the subject may be subjected to screening or suitability testing to determine if the subject is a suitable candidate for pain management therapy using the BCI based systems and methods described in this document. Such screening and suitability testing may include a decorrelation test designed to assess whether brain signals produced by the subject for certain defined imagined or real intentions decorrelate from brain signals produced with the subject in a "rest" state, and as such, use can be made of BCI techniques with the particular subject. A decorrelation test may also include identifying a frequency or other attribute of the brain signals at which decorrelation from rest is found to be present. Screening/suitability tests at 220 may be performed using a feedback device, for example device 140 as described in connection with FIG. 1, and without using a stimulation device 150.

At 230, a BCI training session may be conducted, utilizing a stimulation device, such as stimulation device 150 shown in FIG. 1, positioned in a location that is local to the source of pain and/or located such that is within the pain pathway of the source of pain. The BCI training session at 230 may also be done using a feedback device such as device 140 as shown in FIG. 1. This BCI training session of 230 is done to ascertain, for the particular subject, the defined brain signals that will assist the subject in managing and/or relieving pain. The brain signal information that may be evaluated at 230 may include, for example, (1) location information associating certain ones of the acquired brain signals to a particular electrode location, wherein each of the electrodes may be positioned on the subject and identified within the software of the control/processing module 120 to be indicative of a particular region and location of the brain; (2) frequency information regarding a frequency and/or range of frequencies for the acquired brain signals at each electrode/brain location, wherein the frequency information may correspond, for example, to various known types of brain rhythms (for example, alpha rhythm brain waves having a frequency range of 8-12 Herz, which range is understood to bridge a gap between conscious thinking and the subconscious mind; beta rhythm brain waves having a frequency range of 12-40 Herz, which range is understood to be involved in conscious thought, logical thinking, and tend to have a stimulating effect; etc.); and (3) a magnitude or power level of the brain signals at each of multiple different frequencies or frequency ranges.

The process at 230 may result in ascertaining and saving in the memory of the BCI control/processing device the particular brain signals (electrodes, frequencies or frequency ranges, and power levels) that will assist the subject in managing and/or relieving pain. Later during therapy sessions these defined brain signals may be used as part of the BCI training process (comparing brain signals the subject produces in a therapy session to the defined brain signals found during 230 and stored in memory of a BCI control/processing module.

Next at 240 BCI pain management therapy session(s) may be performed to train a subject to produce certain defined brain signals to relieve pain. Detail of two examples of how the therapy session 240 may be performed is addressed in FIGS. 3A and 3B. A therapy session of 240 may be done once or multiple times (for example, periodically such as once a day or once a week), depending on how the subject responds to such therapy session. The therapy session of 240 may begin with a calibration step at 242 to ascertain whether or not the defined brain signals may need to be updated, owing to elasticity of the brain and evolution of the nature of brain signals that may be produced over the course of one or more therapy sessions. If at 242 calibration is determined to be needed, the process at 230 may be performed again to identify the current brain signals that will assist the subject in managing and/or relieving pain. If no calibration is determined to be needed at 242, or the defined brain signals have been updated, then at 244 the therapy session may be conducted—utilizing the stimulation device such as device 150 in FIG. 1 and/or a feedback device 140 as shown in FIG. 1—to train the subject to produce the defined brain signals to manage and/or relieve pain.

Figure 3A:
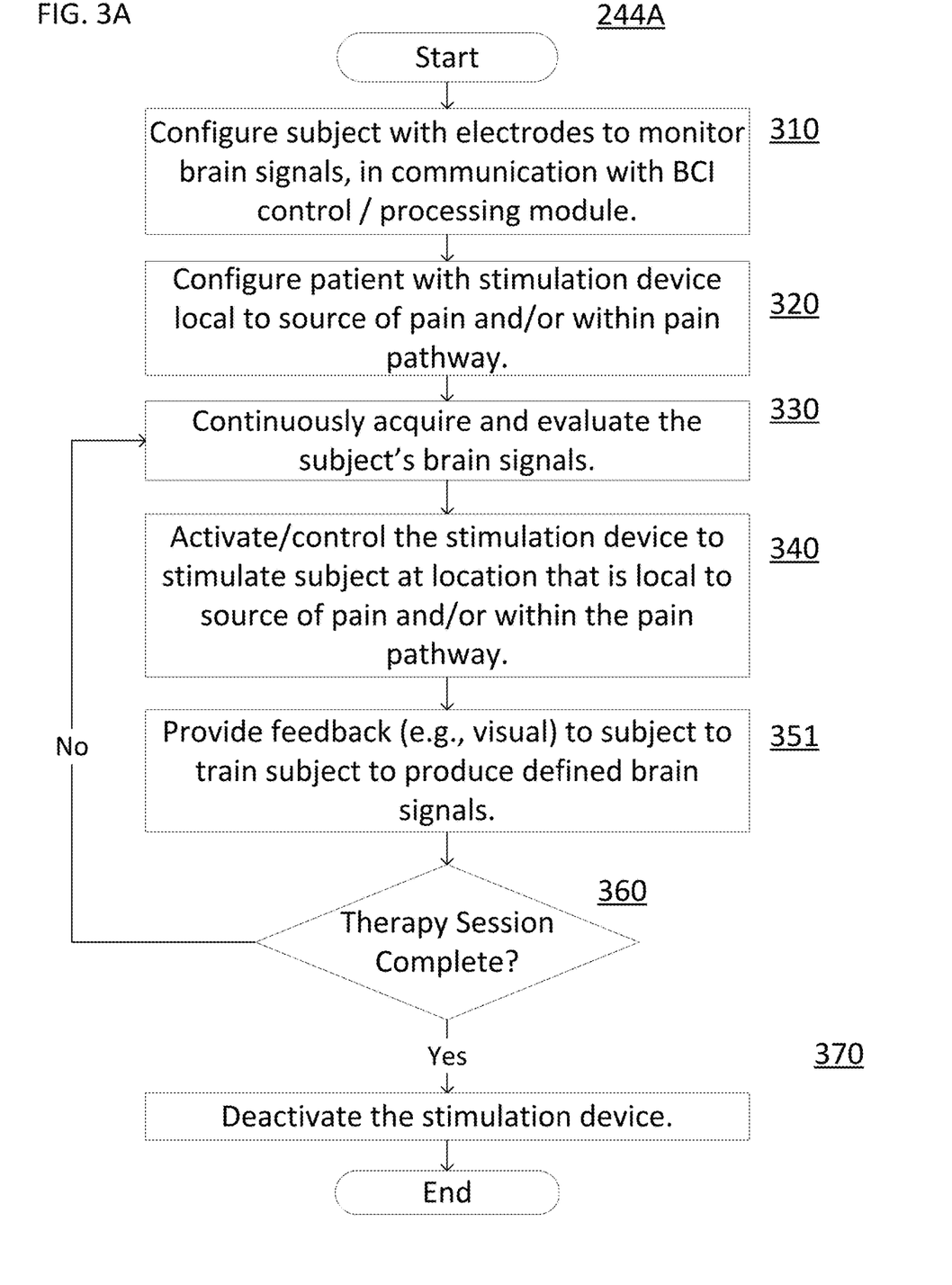
FIGS. 3A and 3B are flowcharts illustrating two different embodiments of a method for conducting a therapy session to train a subject to produce defined brain signals to manage and/or relieve pain, which method may be utilized in the method of FIG. 2.
Figure 3B:
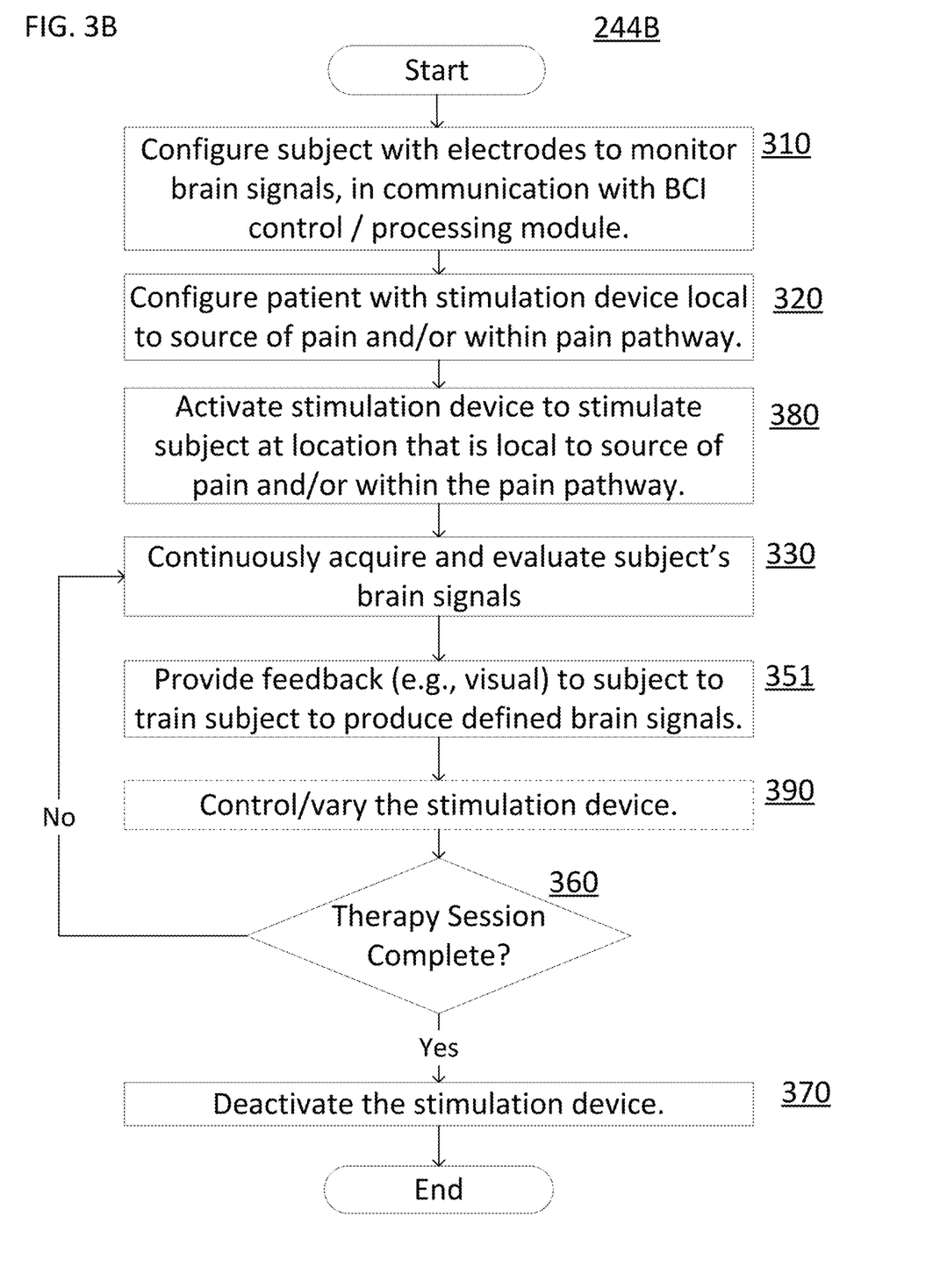
Figure 3C:
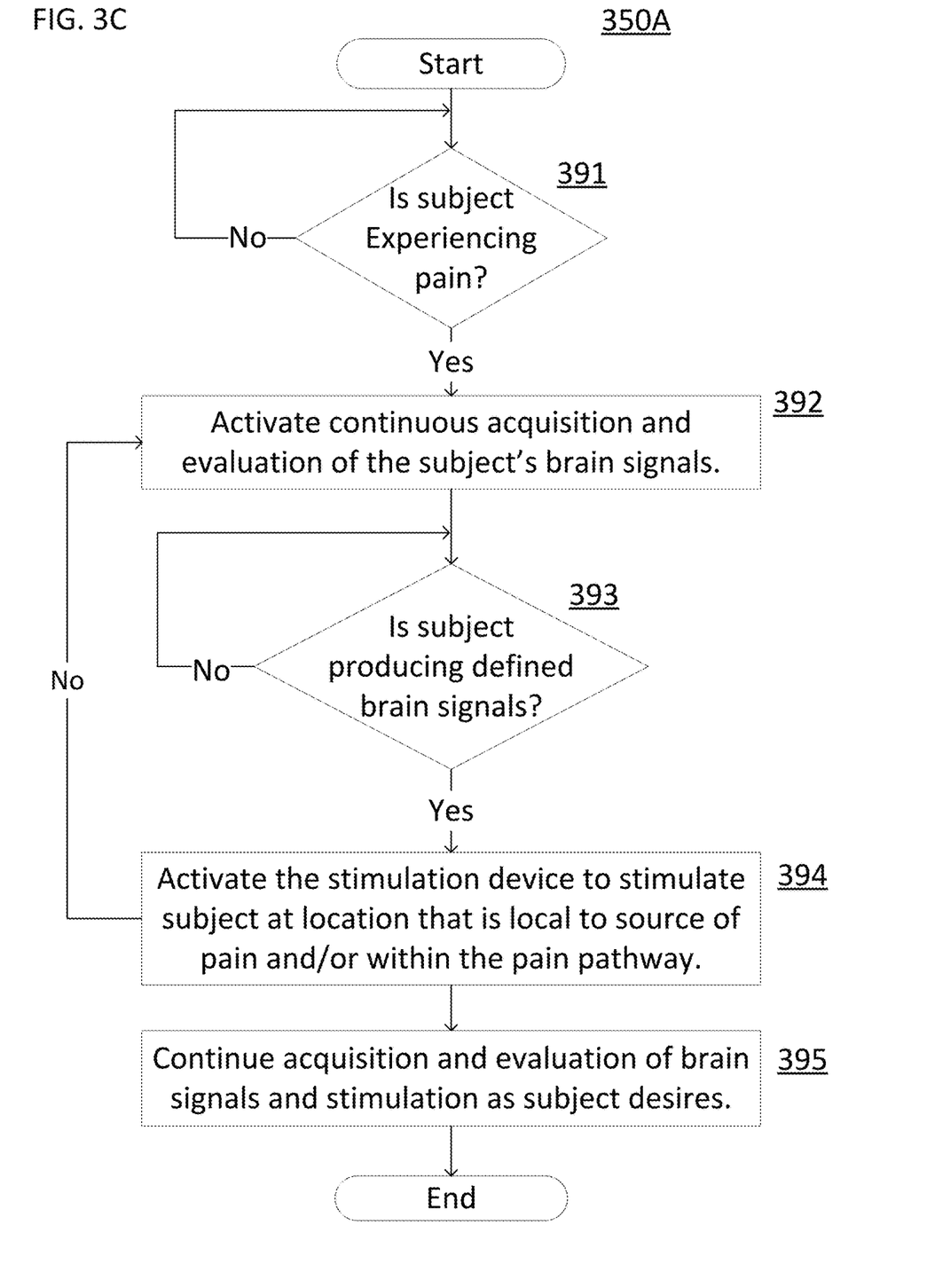
FIG. 3C is a flowchart illustrating an embodiment of a method a subject may use when sensing pain to assist the subject in managing or relieving pain, which method may be utilized in the method of FIG. 2.

Next at 250, optionally, the subject may also be assisted in generating brain signals over the normal course of the day to manage and/or relieve pain that may arise, for example, using the method disclosed in FIG. 3C. In some embodiments, the process at 250 may utilize a stimulation device such as device 150 shown in FIG. 1. In other embodiments, such a stimulation device may not be utilized in the method of 250, but simply rely upon bodily processes resulting from the generation of the defined brain signals to relieve and/or manage pain when generated by the subject.

The system components of FIG. 1 may be used in various implementations of the general method shown in FIG. 2 under various different scenarios. For example, in a first scenario, the stimulation device 150 may be a cold temperature device that utilizes, for example, a Peltier cooling device. The cold temperature stimulation device is intended to supply the subject with an uncomfortable or painful stimulus signal. The stimulation device 150 may be positioned or worn on the subject's body during a BCI pain management therapy session at a location that is local to the source of pain, or in other words, within the pain pathway of the source of pain. For example, for a subject experiencing pain in the wrist and hand associated with carpel tunnel syndrome, the stimulation device may be placed on the forearm of the subject near the subject's wrist.

In this first scenario, the pain management therapy session may consist of a BCI system used in conjunction with a cold temperature stimulation device producing a sense of pain or discomfort near a source of pain and/or within the pain pathway. The objective of the pain management therapy session is to train the patient to produce an increase in power in alpha rhythm brain power when thereafter the subject is experiencing pain. Alpha rhythm brain waves have a frequency range of 8-12 Herz, which range is understood to bridge a gap between conscious thinking and the subconscious mind. By contrast, beta rhythm brain waves have a frequency range of 12-40 Herz, which range is understood to be involved in conscious thought, logical thinking, and tend to have a stimulating effect. The subject being able to produce an increase in the power of the alpha rhythm brain waves may produce in the subject enhanced inhibition of the pain stimuli as that stimuli is being received at the brain, and as such help to manage and/or relieve the pain. It is believed that conducting a BCI based pain management therapy session in this manner utilizing a stimulation device will help solidify or galvanize the training process so that the patient is better able thereafter to produce the desired brain signals (e.g., an increase in power in alpha rhythm brain signals) to manage and/or relieve pain.

In a second scenario, the stimulation device 150 used in conjunction with a BCI system may be a vibrational device. The vibrational device is intended to supply the subject with a comfortable and/or soothing stimulus signal. As with the first scenario, the stimulation device 150 may be positioned or worn on the subject's body near the source of pain and/or in the pain pathway during a BCI pain management therapy session. In this scenario, the BCI pain management therapy session may consist of the vibrational stimulation device being used during a BCI training session to train the patient to produce a decrease in power in alpha rhythm brain power when thereafter the subject is experiencing pain. The subject being able to produce a decrease in the power of the alpha rhythm brain waves may produce in the subject enhanced excitability of the motor cortex and would gate painful input to the thalamus of the brain, and as such help to manage and/or relieve the pain. Here again, it is believed that conducting a BCI based pain management therapy session in this manner utilizing a stimulation device will help solidify or galvanize the training process so that the patient is better able to produce thereafter the desired brain signals (e.g., a decrease in power in alpha rhythm brain signals) to manage and/or relieve pain.

Turning now to FIG. 3A, further detail is provided regarding a first example of a therapy session (244A) that may be utilized for the therapy session 244 in the method of FIG. 2. In the example therapy session (244A) shown in FIG. 3A, at 310 the subject is configured with electrodes to monitor the subject's brain signals. The electrodes so configured may be part of the brain signal acquisition system 130 (EEG headset) shown in FIG. 1 or alternatively may be implantable electrodes configured to be directly adjacent the brain under the skull as described above. The electrodes so configured would be in communication with a BCI control/processing module, such as the module 120 shown in FIG. 1. Communication between the electrodes and a BCI control/processing module may be accomplished with wireless transmissions between a brain signal acquisition system 130 and the BCI control/processing module 120.

At 320, the subject is further configured with a stimulation device that is positioned at a location on the subject's body that is local to the source of pain. As with the case illustrated in FIG. 1, the stimulation device may be a wearable patch type device 150 that may be applied to and worn by the patient. Such a wearable patch type stimulation device 150 may include a transmitter/receiver (e.g., a wireless transmitter/receiver, such as a Bluetooth™ classic or low energy communications module) to enable wireless or wired communication between a BCI control/processing module 120 and the stimulation device 150. The stimulation device may be, in various embodiments, a hot-cold generating device, a vibrational device, etc., as discussed above.

Commencing at 330, the BCI pain management therapy session begins. At 330, the subject's brain signals are continuously acquired and evaluated. Acquisition of the brain signals to perform such evaluation may be accomplished, for example, by the brain signal acquisition system 130 shown in FIG. 1, which may acquire electrical information from each of the multiple electrodes and may additionally perform front-end processing functions on that acquired electrical information. The brain signal acquisition system 130 may then continuously transmit wirelessly the processed brain signal information—in real-time or in other words as that information is acquired and as it is changing—to a BCI control/processing module such as module 120 in FIG. 1, which then may evaluate the brain signal information on a continuous basis to determine the nature of the brain signals that the subject has produced so that appropriate visual or other feedback may be provided to the subject as part of the BCI training process.

The brain signal information that is evaluated by a BCI control processing module such as module 120 in FIG. 1 may include, for example, (1) location information associating certain ones of the acquired brain signals to a particular electrode location, wherein each of the electrodes may be positioned on the subject and identified within the software of the control/processing module 120 to be indicative of a particular region and location of the brain; (2) frequency information regarding a frequency and/or range of frequencies for the acquired brain signals at each electrode/brain location, wherein the frequency information may correspond, for example, to various known types of brain rhythms (for example, alpha rhythm brain waves having a frequency range of 8-12 Herz, which range is understood to bridge a gap between conscious thinking and the subconscious mind; beta rhythm brain waves having a frequency range of 12-40 Herz, which range is understood to be involved in conscious thought, logical thinking, and tend to have a stimulating effect; etc.); and (3) a magnitude or power level of the brain signals at each of multiple different frequencies or frequency ranges.

At 340 and depending on the results of the evaluation of the brain signals performed at 330, the stimulation device that has been applied to the subject at a location local to the source of pain and/or within the pain pathway may be activated and/or controlled in a certain manner depending upon the brain signal evaluation. For example, in an embodiment wherein the stimulation device is a cold temperature generating device (for example, employing a Peltier device to controllably create a cold temperature of a specified temperature level), the stimulation device may be activated to a particular temperature level. Then, as the subject produces brain signals that become closer to certain defined brain waves that will provide pain relief to the subject after the therapy session, the stimulation device may become progressively colder. This stimulation may serve to solidify or galvanize the BCI training for the subject to produce the desired brain signals when the subject feels pain after the therapy session.

At 351, optionally the method may include, in addition to feedback provided by a stimulation device at 340, additional feedback for example visual feedback to the subject designed to help train the subject produce the desired brain signals that will help the subject manage and relieve pain after the therapy session has been completed. As discussed above for example, the BCI feedback device 140 may provide various visual displays useful in training the patient to produce certain desired brain signals, such as those commonly used in the BCI field (e.g., cursor or object location on a video screen and movement of that cursor/object) or that may be developed in the future. In various embodiments, the feedback device 140 may provide other forms of feedback such as auditory (sound) feedback signals and/or haptic feedback signals (e.g., vibrational, motion or other forces sensed by the subject's sense of touch).

As indicated by the decision block 360 of the FIG. 3A flowchart, the therapy session may continue to occur with brain signals being continuously acquired and evaluated (330), the stimulation device continuously being controlled (340), and the optional feedback provided to the subject (340) being continually updated, or the therapy session may be ended at any time. If a decision has been made at 360 to end the therapy session, at 370 the stimulation device may be deactivated.

Following the therapy session 244A, the brain signal and activation system and stimulation device may, in some embodiments, be removed from the subject after the therapy session. Alternatively, the brain signal acquisition system and in some implementations also the stimulation device may be utilized after the therapy session, in combination, for example with a wearable BCI control/processing module, to utilize BCI techniques to manage and/or relieve pain after the therapy session is complete, for example, during the course of the subject's daily route separate from therapy, an example of which will be described later in connection with FIG. 3C.

Turning now to FIG. 3B, further detail is provided regarding a second example of a therapy session (244B) that may be utilized for the therapy session 240 in the method of FIG. 2. As with the FIG. 3A method, in FIG. 3B at 310 the subject is configured with electrodes to monitor the subject's brain signals, and the subject is configured with a stimulation device that is positioned at a location on the subject's body that is local to the source of pain and/or within the pain pathway. The stimulation device may be, in various embodiments, a hot-cold generating device, a vibrational device, etc., as discussed above.

Commencing at 380, the BCI pain management therapy session begins. At 380 the stimulation device is activated at the start of the therapy session, at which time the subject is subjected to the stimulation provided by the stimulation device (e.g., uncomfortable hot or cold temperature; soothing vibrational input, etc.). Then, at 330, the subject's brain signals are continuously acquired and evaluated, as with the FIG. 3A method. Next at 351 and depending on the results of the evaluation of the brain signals performed at 330, feedback such as for example visual feedback may be provided to the subject. Such feedback is designed to help train the subject to produce the desired brain signals so as to help the subject manage and relieve pain after the therapy session has been completed. As discussed above for example, a BCI feedback device such as the device 140 shown in FIG. 1 may provide various visual displays useful in training the patient to produce certain desired brain signals, such as those commonly used in the BCI field (e.g., cursor or object location on a video screen and movement of that cursor/object) or that may be developed in the future. In various embodiments, the feedback device 140 may provide other forms of feedback such as auditory (sound) feedback signals and/or haptic feedback signals (e.g., vibrational, motion or other forces sensed by the subject's sense of touch).

At 340, in addition to the feedback provided by separate feedback device from the stimulation device at 351, the stimulation device that has been applied to the subject at a location local to the source of pain and/or within the pain pathway may be controlled in a certain manner, depending upon the brain signal evaluation for example, to vary the output (e.g., adjust the temperature device to be warmer or colder, alter the magnitude of vibration in a vibrational device, etc.). For example, in an embodiment wherein the stimulation device is a cold temperature generating device (for example, employing a Peltier device to controllably create a cold temperature of a specified temperature level), the stimulation device may be activated to a particular temperature level than the temperature level to which the device had previously been adjusted. In one example, as the subject produces brain signals that become closer to certain defined brain waves that will provide pain relief to the subject after the therapy session, the stimulation device may become progressively colder. This feedback provided by the adjustment of the stimulation device during the therapy session may serve to solidify or galvanize the BCI training for the subject to produce the desired brain signals when the subject feels pain after the therapy session.

As indicated by the decision block 360 of the FIG. 3A flowchart, the therapy session may continue to occur with brain signals being continuously acquired and evaluated (330), the stimulation device continuously being controlled (340), and the optional feedback provided to the subject (340) being continually updated, or the therapy session may be ended at any time. If a decision has been made at 360 to end the therapy session, at 370 the stimulation device may be deactivated.

As with the FIG. 3A method (244A), following the therapy session 244B of FIG. 3B the brain signal and activation system and the stimulation device may, in some embodiments, be removed from the subject after the therapy session. Alternatively, the brain signal acquisition system and optionally also the stimulation device may be utilized after the therapy session, in combination for example with a wearable BCI control/processing module, to utilize BCI techniques and optionally also the stimulation device to manage and/or relieve pain after the therapy session is complete, for example, during the course of the subject's daily route separate from therapy, an example of which will be described in connection with FIG. 3C.

Turning now to FIG. 3C, a method 350 is described which may serve as the process at 250 in the method of FIG. 2. Generally in the method of 350 the brain signal acquisition system and a stimulation device is utilized after one or more therapy sessions, in combination for example with a wearable BCI control/processing module, to utilize BCI techniques and the stimulation device to manage and/or relieve pain after one or more therapy sessions are complete, for example, during the course of the subject's daily route separate from therapy. In method 350, the subject is configured with a brain signal acquisition system, a BCI control/processing module (for example, a BCI module that is wearable by the subject), and a stimulation device.

If it is determined at 391—by the subject him or herself for example—that the subject is experiencing pain, at 392 continuous acquisition and evaluation of the subject's brain signals may be activated. The activation may occur by manually controlling one or more activation switches to activate the brain signal acquisition system and the BCI control/processing module. Such activation starts an on-going (real time) evaluation of the brain signal's that the subject is producing, as acquired by a brain signal acquisition system such as an EEG headset as shown in FIG. 1.

At 393, it is continuously evaluated at 393 whether the subject is producing the certain defined brain signals, for example, whether a threshold level in change has been met with respect to a certain frequency or frequencies of brain signals as compared to a rest condition. If it is determined that the subject is producing the defined brain signals (e.g., the threshold is met), then at 394 the stimulation device may be activated to stimulate the subject where the stimulation device is positioned, namely, at a location that is local to the source of pain and/or within the pain pathway. In this example, the stimulation device may be a device that provides a comforting or soothing sensation (e.g., a vibrational device). The BCI processing/control module may be configured to activate and control the stimulation device, and as such, the method at 394 may be accomplished by the BCI processing/control module activating the stimulation device. In this example, the activation of the stimulation device may serve both to provide feedback to the subject indicating that the subject is in fact producing the defined brain signals that may assist in managing and/or relieving pain as discussed previously and to provide an additional comforting or soothing sensation to the subject at or near the location of the source of pain to additionally help manage and/or relieve the pain.

As indicated at 395, the continuous acquisition and evaluation of brain signals (392) and use of the stimulation device if and when the subject is producing the defined brain signals (393 and 394) may continue as the subject desires. When the subject desires, the system and devices may be deactivated, for example, by the subject manually activating one or more deactivation switches.

Figure 4:
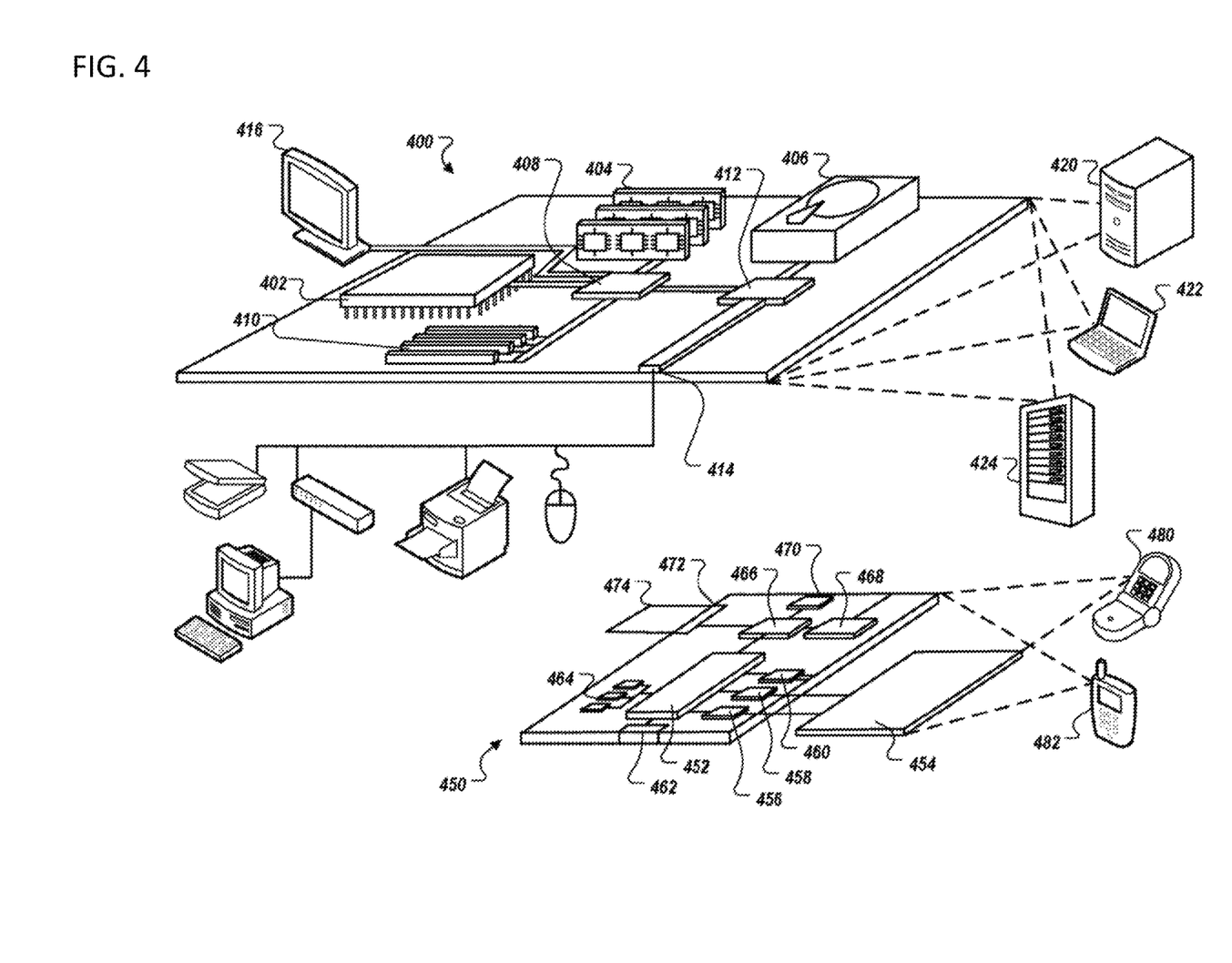
FIG. 4 is a block diagram illustrating computing systems, components and devices that may be utilized in the systems, devices and methods for managing pain as described herein.

FIG. 4 is a block diagram of computing devices 400, 450 that may be used to implement the systems and methods described in this document (for example, the systems and methods included in the BCI processing/control module 120 of FIG. 1, as either a client or as a server or plurality of servers. Computing device 400 is intended to represent various forms of digital computers, such as laptops, desktops, workstations, personal digital assistants, wearable computing devices, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high-speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 400. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, or memory on processor 402.

The high-speed controller 408 manages bandwidth-intensive operations for the computing device 400, while the low speed controller 412 manages lower bandwidth-intensive operations. Such allocation of functions is an example only. In one implementation, the high-speed controller 408 is coupled to memory 404, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. Additionally, the processor may be implemented using any of a number of architectures. For example, the processor may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provided, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, or memory on processor 452 that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Additionally computing device 400 or 450 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

A number of embodiments of the invention have been described. Nevertheless, it will be understood that various modifications may be made without departing from the spirit and scope of the invention. Accordingly, other embodiments are within the scope of the following claims.

What is claimed is:

1. A method of conducting a pain management therapy session, comprising:
    applying, to a subject and at a location that is near to a source of pain and/or within a nervous system pain pathway to the source of pain, a single stimulation device, wherein the stimulation device is in signal communication with a brain computer interface ("BCI") control system;
    using a brain signal acquisition system with skin surface electrodes to continuously acquire brain signals from the subject's brain;
    transmitting the brain signals to the BCI control system;
    evaluating, by the BCI control system, the brain signals in comparison to an alpha brain rhythm;
    applying, by the stimulation device and as a neurofeedback response to an evaluation of the brain signals in comparison to the alpha brain rhythm, a single stimulus to the subject at the location that is near to the source of pain and/or within the nervous system pain pathway to the source of pain; and
    receiving results of a decrease in power of alpha rhythm brain waves produced by the subject.

2. The method of claim 1, wherein the single stimulus applied to subject by the stimulation device comprises a proprioceptive stimulus.

3. The method of claim 1, wherein the single stimulus applied to the subject by the stimulation device is generated by a vibration generating element of the stimulation device.

4. The method of claim 3, wherein the vibration generating element is a wearable vibration generating element.

5. The method of claim 1, comprising:
    training the subject before conducting the pain management therapy session to obtain the alpha brain rhythm of the subject.

6. The method of claim 1, comprising determining suitability of the subject for pain management therapy before conducting the pain management therapy session with the subject.

7. The method of claim 6, wherein determining suitability comprises performing a decorrelation test on the subject.

8. The method of claim 1, wherein applying the single stimulus is used to train the subject to manage pain.

9. A system for conducting a pain management therapy session, comprising:
    a brain signal acquisition system for continuously acquiring brain signals from a a subject's brain;
    a single stimulation device configured and adapted to be applied to the subject at a single location within a pain pathway of a source of pain; and
    a brain computer interface ("BCI") control/processing module programmed to:
        receive the brain signals;
        evaluate the brain signals in comparison to an alpha brain rhythm;
        in response to the evaluation of the brain signals in comparison to the alpha brain rhythm, cause an activation of the stimulation device to generate a single stimulus to train the subject; and
        receive results of a decrease in power of alpha rhythm brain waves produced by the subject.

10. The system of claim 9, wherein the stimulation device is configured to activate in response to neurofeedback of the subject.

* * * * *

UNITED STATES PATENT AND TRADEMARK OFFICE
CERTIFICATE OF CORRECTION

PATENT NO. : 12,370,340 B2  
APPLICATION NO. : 16/521056  
DATED : July 29, 2025  
INVENTOR(S) : Kern Bhugra and Eric C. Leuthardt Page 1 of 1

It is certified that error appears in the above-identified patent and that said Letters Patent is hereby corrected as shown below:

In the Claims

In Column 16, Line 28 (Approx.), In Claim 9, delete "a a" and insert -- a --.

Signed and Sealed this  
Thirtieth Day of September, 2025

John A. Squires  
*Director of the United States Patent and Trademark Office*